United States Patent [19]

Wozniak et al.

[11] Patent Number: 4,781,683

[45] Date of Patent: Nov. 1, 1988

[54] SINGLE-USE, SELF-ANNULLING INJECTION SYRINGE

[75] Inventors: John J. Wozniak, Columbia; Kam Leong, Perry Hall, both of Md.

[73] Assignee: The Johns Hopkins University, Baltimore, Md.

[21] Appl. No.: 41,036

[22] Filed: Apr. 22, 1987

[51] Int. Cl.⁴ .............................................. A61M 5/00
[52] U.S. Cl. .................................... 604/110; 604/236
[58] Field of Search ............... 604/187, 190, 218, 236, 604/238, 110, 319–321, 212, 215; 137/197, 199; 128/765

[56] References Cited

U.S. PATENT DOCUMENTS

| 2,467,217 | 4/1949 | Mikeska | 137/197 |
| 2,601,216 | 6/1952 | White et al. | 137/197 |
| 3,757,779 | 9/1973 | Rovinski | 604/190 |
| 3,768,478 | 10/1973 | Fertik et al. | 604/320 |
| 3,850,348 | 11/1974 | Bessot et al. | 604/236 |
| 3,982,538 | 9/1976 | Sharpe | 604/320 |
| 4,207,870 | 6/1980 | Eldridge | 137/197 |
| 4,226,236 | 10/1980 | Genese | 604/89 |

Primary Examiner—Dalton L. Truluck
Assistant Examiner—Denise Whelton
Attorney, Agent, or Firm—Robert E. Archibald; Howard W. Califano

[57] ABSTRACT

A single-use, self-annulling syringe is disclosed that is rendered inoperative after a single use without requiring any deliberate action on the part of a user. The injection device uses a hydrophilic expansion plug positioned in the outlet flow channel of the syringe, which expands a short time after being exposed to a drug containing water, thereby rendering the syringe inoperative.

16 Claims, 2 Drawing Sheets

A              B

SINGLE-USE, SELF-ANNULLING INJECTION SYRINGE

BACKGROUND OF THE INVENTION

1. Field of the Invention

The present invention relates to a single use, self-annulling syringe that is rendered inoperative after a single injection without requiring any deliberate action on the part of the user. Passive inactivation is desirable to eliminate syringe/needle reuse which has been identified as a source for spreading blood-transmitted infectious diseases.

2. Description of the Prior Art

In both the United States and particularly in third world countries, multiple use of unsterile needles and unsterile syringes can transmit infectious agents including hepatitis viruses and LAV/HTLV-III, a virus which causes the acquired immunodeficiency syndrome (AIDS).

The prior art teaches various methods and apparatuses for breaking off and storing the needle portion of the syringe so that the syringe cannot be reused. The following U.S. patents are illustrative of this technique: U.S. Pat. Nos. 3,306,291; 3,796,359; 3,893,608; 4,121,588; 4,220,151; 4,266,544; 4,270,536; and 4,333,457. However, for these syringes to be single use, action (e.g., breaking off the needle tip) must be taken by the medical staff. Public health researchers have found that medical staff, particularly in third world countries, are not taking the action necessary to render these syringes inoperative. Therefore, passive inactivation of the syringe is desirable—that is, a syringe that is rendered inoperable without requiring any deliberate action, (e.g., breaking the needle) on the part of the user or the medical staff.

The prior art also teaches various syringes having a means for destroying the syringe cylinder during the injection stroke. U.S. Pat. Nos. 3,667,657; 3,951,146; 3,998,224 and 4,391,273 issued to Marcello Chiquiar-Arias teach the use of a syringe piston that contains a sharpened portion which destroys the syringe cylinder during downstroke. In U.S. Pat. No. 3,667,657 a knife edge attached to the piston cuts through the syringe cylinder. In U.S. Pat. No. 3,951,146 the knife edge is mounted with a spring mechanism allowing the piston to initially draw fluid into the syringe with the knife edge remaining in a recessed position. U.S. Pat. Nos. 3,998,224 and 4,391,273 teach a punching element mounted on the bottom of the piston for piercing the syringe cylinder when the piston is pressed in a downward position. Using a similar technique in U.S. Pat. No. 4,062,287, the forward edge of the syringe cylinder wall and the lower end of the plunger wall have mating surfaces. These surfaces mate when the plunger is pressed into its most downward position. Once the surfaces have mated, motion of the plunger will cause the end walls to break away from the barrel.

Certain other syringes appearing in the prior art utilize a locking means to prevent multiple use. U.S. Pat. No. 3,478,937, issued to I. Solowey, teaches two embodiments of a mechanical locking mechanism. In the first embodiment, a flexible disk flexes to pass through the central opening of the syringe during the downstroke of the plunger. Once through the central opening, the flexible disk is shaped so that it can no longer pass through the central opening during the upstroke of the plunger. Therefore, the syringe can only be used once. In the second embodiment, two pivotal pawls replace the flexible disk. Once the pawls have passed through the central opening they extend outward because of a spring mechanism. Once the pawls are extended, the plunger is inoperative. U.S. Pat. No. 4,233,975, issued to Arthur Yernan, also teaches two embodiments for freezing the motion of the plunger after injection. In the first embodiment, downward motion of the plunger causes a plug element to be pushed forward and locked into a female portion. Once the plug element is so engaged, fluid flow into the hypodermic needle is blocked. In the second embodiment, the piston itself contains a flexible portion that will fill a recess, thereby locking the piston in a downward position. Any attempt to pull the piston from its downward position will cause separation of the piston rod from the piston. Other mechanical locking means are taught in U.S. Pat. Nos. 4,367,738; 4,391,272; 4,493,703; and 4,252,118.

U.S. Pat. No. 3,874,383, issued to John Glowacki, uses a plastic insert made of a heat deformable material that is placed within the lower portion of the syringe cylinder. If any attempt is made to sterilize or autoclave the liner it will heat, distort and shrivel up. In the embodiment shown in FIGS. 1-3 of Glowacki, this would render the syringe inoperative and in the embodiment shown in FIGS. 4-5 of Glowacki would remove the Luer lock flanges so that a second syringe needle cannot be fitted into the hub. However, the Glowacki reference does not prevent reuse of an unsterilized syringe—it merely prevents attempts to sterilize a syringe for a possible second use.

SUMMARY OF THE INVENTION

The present invention provides a single use, self-annulling syringe that is rendered inoperative after a single injection without requiring any deliberate action (e.g., breaking of the needle) on the part of the user or medical staff. The invented syringe uses a hydrophilic expansion plug that is positioned in the fluid channel of the syringe. The hydrophilic expansion plug will swell when exposed to water contained in the medication and will occlude the fluid channel, thereby preventing multiple use of the syringe and needle.

The present invention works equally well with a conventional hypodermic syringe or a hypodermic syringe pre-filled with lyophilized medication. The present invention will also work equally well with either the traditional type piston syringe or a squeezable ampoule syringe.

The invented single use syringe generally includes: (1) a variable volume chamber that is generally provided by a piston reciprocally mounted in a conventional syringe barrel; (2) a hollow injection needle mounted on the syringe forming a flow channel between the variable volume chamber and the internal lumen of the injection needle; and, (3) a hydrophilic expansion means, placed within the flow channel, for blocking the flow channel after being exposed to a medication containing water. Expansion of the plug automatically prevents reuse of the syringe. The swelling kinetics of the hydrophilic expansion means can be controlled by adjusting the cross link density, the composition of the copolymers or hydrogel, the molecular weight of the polymers, and the geometry of the hydrophilic plug means. By so controlling swelling kinetics, the onset of the self-annulling action could be selected to range from a fraction of a minute to several minutes or more.

The principal novel feature of the invention is the placement of a hydrophilic expansion means in the flow channel of the syringe to prevent multiple use. Expansion of the hydrophilic plug automatically renders the syringe inoperative.

A second novel feature is a self-annulling syringe, using a hydrophilic expansion means, that can be used with a syringe preloaded with a lyophilized drug or vaccine.

A third novel feature of this invention is that it allows the user to operate the piston several times. This enables the medical staff to fill the syringe, remove entrapped air, aspirate to establish that the needle is in a blood vessel and then to complete the injection. These steps are normal with traditional syringe operation and thus no retraining of health care personnel is required.

DETAILED DESCRIPTION OF THE PREFERRED EMBODIMENT

Figure 1:
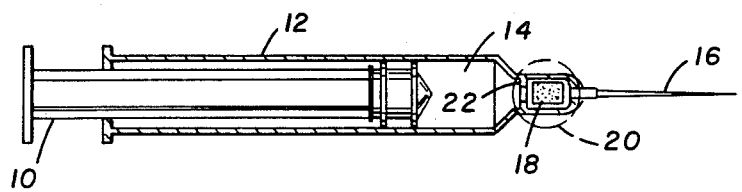
FIG. 1 is a cross-sectional view of a single use, self-annulling syringe as taught by the present invention.

FIG. 1 illustrates an embodiment of the single-use, self-annulling syringe. The syringe is of conventional design having piston 10 reciprocally mounted within a hollow syringe barrel to form a variable volume chamber 14 for injecting medication through a hollow needle 16 into a patient. The point of novelty is the placement of a hydrophilic expansion plug 18, made from a biological inert polymer, in the flow channel between the variable volume chamber 14 and the needle 16. As shown in FIG. 1, the hydrophilic expansion plug 18 is confined to the syringe nozzle region 20 by baffle 22, and in its unexpanded state does not block fluid flow. The syringe is used in a normal fashion to draw medication from a vial and inject it into the patient. However, after a short period of time the hydrophilic plug absorbs water from the residual in the syringe and swells to occlude the nozzle and render the syringe inoperable.

The period of time from introduction of liquid into the syringe to expansion of the hydrophilic plug, rendering the syringe inoperative, can range from 30 seconds to 30 minutes or larger, by choice of material for the hydrophilic plug. The swelling kinetics of hydrophilic polymers can be controlled by adjusting the cross linked density (in some materials), the composition of the copolymers, and the molecular weight. The hydrophilic expansion plug can be made from a host of hydrophilic swellable polymers or hydrogels. A partial, but not limiting list, of biocompatible polymers useful for this purpose includes: cross linked poly (vinyl alcohol), cross linked poly (ethylene oxide), poly (acrylamide), poly (N-vinyl pyrrolidone), poly (2-hydroxyethyl methacrylate) and methyl cellulose. Besides varying the types of polymers, other variables that control the available operating time of the syringe are the thickness and shape of the swelling polymer. Additionally, the use of certain radiation cross-linked polymers having viscoelastic memory (U.S. Pat. No. 3,419,006) can insure that the plug remains in an expanded state after a single use even if attempts are made to dehydrate the material.

Figure 2:
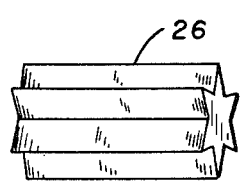
FIGS. 2A and 2B show enlarged views of two embodiments of the hydrophilic expansion plug.
Figure 2:
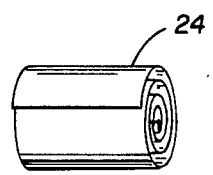

FIGS. 2A and B are enlarged views of two embodiments of the hydrophilic expansion plug. The hydrophilic plug can be made from a small strip of hydrophilic polymeric material or hydrogel wound into a spiral 24. Alternatively, the hydrophilic plug can be made from a hydrophilic polymer or hydrogel molded or extruded into a solid shape such as a star-shaped hydrophilic plug 26. It is of course to be understood that various solid shapes can be used other than the star-shaped shown.

As an experimental example, Applicants confined a spiral hydrophilic plug in the syringe nozzle region of a conventional 3cc syringe. The hydrophilic plug was formed from a small strip (0.25 mm thick, 3 mm high and 25 mm long) of polyethylene oxide (PEO) cross-linked with ionizing radiation. The method of cross-linking a polymer with ionizing radiation is known in the art. The cross linked PEO strip, was wound to form a spiral plug similar to that shown in FIGS. 2A and B. The modified syringe was found to initially function normally with fluid being drawn into the piston and injected through the needle. The needle was then set aside for approximately 5 minutes and it was found that the syringe was no longer functional, demonstrating the self-annulling action. Since the full dose of fluid was expelled with the operation of the syringe, only the water residual in the syringe nozzle was needed to fully expand the PEO hydrophilic spiral. Repeated checks over a two-week period had shown the syringe to remain inoperable.

Figure 3:
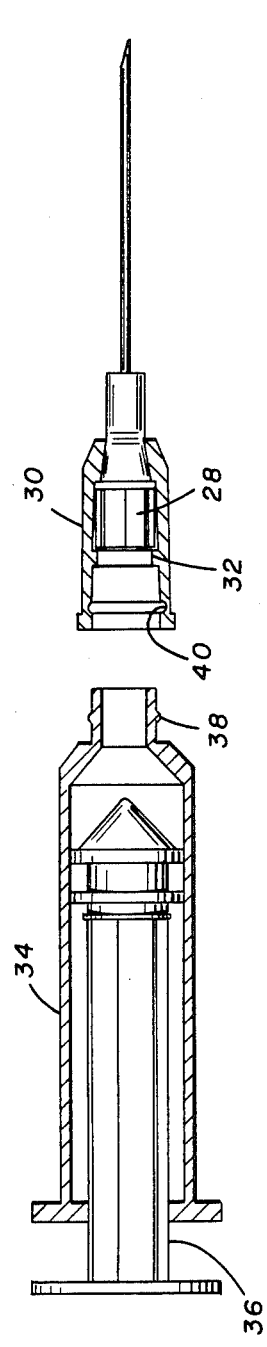
FIG. 3 is a cross-sectional view of a single use, self-annulling syringe with a separate needle body.

FIG. 3 is a cross-sectional view of a single use, self-annulling syringe with a separable needle body. In this embodiment, the hydrophilic expansion plug 28 is located in a separate needle body 30. A step 32 in the needle body 30, is used to secure the hydrophilic expansion plug 28. There is sufficient elasticity in the step 32 and plug 28 to enable the plug to be press fit passed the step nd locked into place. The syringe body 34 is of conventional design having a reciprocally mounted piston 36. A small protuberance 38 on the nozzle portion of the syringe is adapted to mesh with a small notch 40 molded into the separable needle body in order to help hold the needle onto the syringe. The resulting fit would require slight to moderate effort to separate the used needle from the syringe. In operation, the needle body 30 is secured to the syringe body 34 and the syringe is used in a conventional manner. The hydrophilic plug 38 will expand within a preselected reaction time thereby preventing reuse of the needle body.

Figure 4:
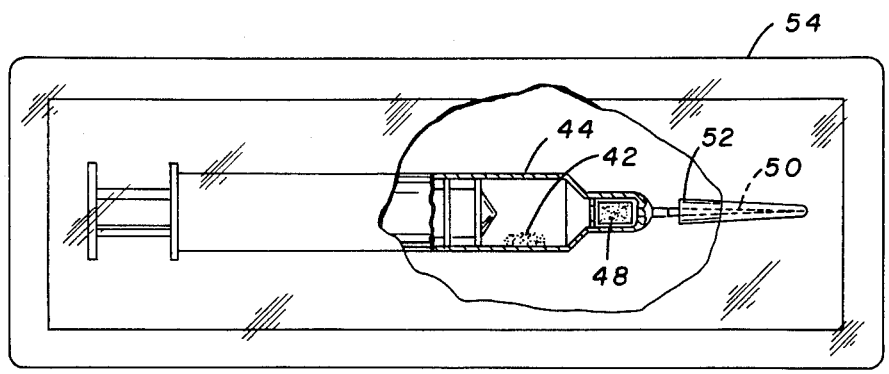
FIG. 4 is a partial cross-sectional view of a single use, self-annulling syringe that is pre-filled with a lyophilized drug or vaccine.

FIG. 4 is a partial cross-sectional view of the single use self-annulling syringe pre-filled with a lyophilized drug. It is common in the third world countries to have a syringe pre-filled with a lyophilized vaccine (i.e., powered vaccine). The syringe is then used to draw diluent, generally sterile water, into the syringe to reconstitute the vaccine in the syringe. The reconstituted vaccine is then injected into the patient. The lyophilized drug 42 is positioned in the syringe 44. The hydrophilic expansion plug is positioned in the nozzle of the syringe in the flow channel from the variable volume chamber to the internal lumen of the needle. The hydrophilic expansion plug has a tailored expansion lapse time to allow sufficient time for the lyophilized drug to reconstitute with diluent and sufficient time for injection in the patient before self-annulling occurs. The needle 50 may fit into a protective cover 52 and the entire syringe may be placed in a sealed pouch 54 during storage. The sealed pouch 54 would prevent exposure of the hydrophilic expansion plug and the lyophilized drug to moisture in the air. The sealed pouch 54 may be made of Mylar ®, but other appropriate materials may be substituted.

Figure 5:
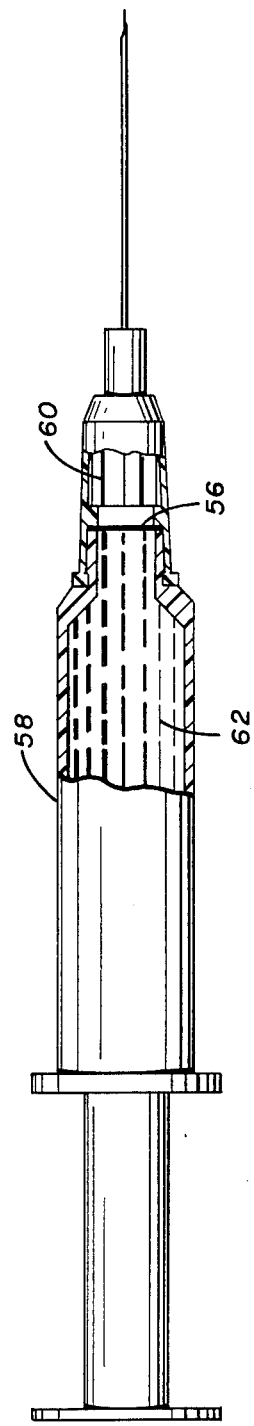
FIG. 5 is a partial cross-sectional view of a single use, self-annuling syringe that is pre-filled with a liquid drug or vaccine.

It must also be understood that the present invention can be practiced with other embodiments than those shown. The conventional syringe having a hollow barrel and reciprocally mounted piston, can be replaced by any variable volume means able to eject medication through the hollow needle. For instance, a squeezable ampoule syringe similar to that shown in U.S. Pat. No. 3,736,933, can provide the variable chamber. As shown in FIG. 5, the insertion of a membrane 56, of Mylar ®, silastic or similar material between the variable volume chamber 58, and the hydrophilic expansion plug 60 (for both the conventional syringe and the squeezable ampoule) syringe would allow the syringe to be pre-filled with a liquid medication 62. The membrane would be designed such that the applied pressure would rupture the membrane allowing fluid to be injecting out through the needle. The hydrophilic expansion plug would then be exposed to the liquid and would expand as taught by the present invention. FIGS. 1, 3 and 4 of the specification merely show the simplest way of locating the hydrophilic expansion plug in the flow channel between the variable volume chamber and the hollow needle. It is to be understood that the hydrophilic expansion plug may be secured in the flow channel in a number of alternative manners.

Obviously, many modifications and variations of the present invention are possible in light of the above teachings. It is therefore to be understood that within the scope of the appended claims the invention may be practiced otherwise than is specifically described.

What is claimed and desired to be secured by Letters Patent of the United States is:

1. A single use injection device, comprising:
   a variable volume chamber adapted to receive a drug containing water;
   an injection needle having an internal lumen, said injection needle connected to said variable volume chamber forming a flow channel between said variable volume chamber and said internal lumen of said injection needle; and
   a hydrophilic expansion means composed essentially of a hydrogel, positioned within said flow channel, for expanding and blocking said flow channel after being exposed to said drug containing water, thereby preventing reuse of the injection device, wherein said hydrophilic expansion means comprises a delay means for providing a preset time window greater than thirty seconds from the time of exposure of said hydrophilic expansion means to said drug containing water for injection of the drug before the hydrophilic expansion means blocks said flow channel.

2. The injection device of claim 1 wherein said variable volume chamber comprises a hollow syringe barrel and a plunger reciprocally mounted within said hollow syringe barrel, said hollow syringe barrel includes an integral tip portion having an internal channel for fixedly connecting said injection needle to said syringe barrel and for providing said flow channel between said syringe barrel and said internal lumen of said injection needle, said hydrophilic expansion means being positioned within said internal channel.

3. The injection device of claim 2, further comprising a step means formed within said internal channel for securing said hydrophilic expansion means within said flow channel.

4. The injection device of claim 2, wherein said hydrophilic expansion means is a polymeric material that is hydrophilic.

5. The injection device of claim 4, wherein said polymeric material is selected from one of:
   poly(vinyl alcohol)
   poly(ethylene oxide)
   poly(acrylamide)
   poly(N-vinyl pyrrolidone)
   poly(2-hydroxyethyl methacrylate)
   methyl cellulose.

6. The injection device of claim 5, wherein said polymeric material is cross-linked.

7. The injection device of claim 2, wherein a lyophilized drug is positioned within said syringe barrel.

8. The injection device of claim 2, wherein a liquid drug is positioned in said syringe barrel and a membrane is positioned across said syringe barrel to separate said liquid drug from said hydrophilic expansion means.

9. The injection device of claim 1, wherein said variable volume chamber comprises a hollow syringe barrel and a plunger reciprocally mounted within said hollow syringe barrel, and wherein said injection device further comprises a connecting means for coupling said injection needle to said syringe barrel, said connecting means comprises:
   a first portion integral to said syringe barrel and forming one end of said syringe barrel; and,
   a second portion fixedly attached to said injection needle and adapted to mate with said first portion, said first and second portions having an internal channel, said hydrophilic expansion means being positioned within said internal channel of said second portion.

10. A single-use injection device comprising:
    a hollow syringe barrel integrally coupled at one end to a narrowed portion having an internal flow channel;
    a plunger reciprocally mounted within said hollow syringe barrel;
    an injection needle having an internal lumen and fixedly mounted into said internal channel; and,
    a hydrophilic expansion means, composed essentially of a hydrogel and positioned within said internal channel, for expanding and blocking said internal channel after being exposed to a drug containing water, thereby preventing reuse of the injection device, wherein said hydrophilic expansion means comprises a delay means for providing a preset time window greater than thirty seconds from the time of exposure of said hydrophilic expansion means to said drug containing water for injection of the drug before the hydrophilic expansion means blocks said internal channel.

11. The injection device of claim 10, further comprising a step projected normal to the axis of said internal channel for securing said hydrophilic expansion means in said internal channel.

12. A single-use injection needle apparatus adapted to couple to the tip portion of a hypodermic syringe, comprising:
- a coupling member adapted to couple to the tip portion of a hypodermic needle, said coupling member having an interior flow channel;
- a needle having an internal lumen fixedly mounted to one end of said coupling member so that said internal lumen is in fluid communication with said interior flow channel; and
- a hydrophilic expansion means composed essentially of a hydrogel, positioned within said interior flow channel, for expanding and blocking said flow channel after being exposed to a drug containing water, thereby preventing reuse of the injection needle apparatus, wherein said hydrophilic expansion means comprises a delay means for providing a preset time window greater than thirty seconds from the time of exposure of said hydrophilic expansion means to said drug containing water for injection of the drug before the hydrophilic expansion means blocks said flow channel.

13. The injection needle apparatus of claim 12, further comprising a step projected normal to the axis of said interior flow channel for securing said hydrophilic expansion means in said flow channel.

14. The injection needle of claim 12, wherein said hydrophilic expansion means is a polymeric material that is hydrophilic.

15. The injection device of claim 14, wherein said polymeric material is selected from one of:
- poly(vinyl alcohol)
- poly(ethylene oxide)
- poly(acrylamide)
- poly(N-vinyl pyrrolidone)
- poly(2-hydroxyethyl methacrylate)
- methyl cellulose.

16. The injection device of claim 15, wherein said polymeric material is cross-linked.

* * * * *